(12) United States Patent
Singhal et al.

(10) Patent No.: US 9,572,590 B2
(45) Date of Patent: Feb. 21, 2017

(54) SURGICAL INSTRUMENT (75) Inventors: Keshav Singhal, Cardiff (GB); Heikki Vilhelm Pitkanen, Helsinki (FI); Nick James Theophilius Metcalfe, Munich (DE)

(73) Assignee: BIOMET UK LIMITED (GB)

( * ) Notice: Subject to any disclaimer, the term of this patent is extended or adjusted under 35 U.S.C. 154(b) by 1324 days.

(21) Appl. No.: 12/444,143

(22) PCT Filed: Oct. 2, 2007

(86) PCT No.: PCT/GB2007/003737
§ 371 (c)(1),
(2), (4) Date: Jul. 9, 2010

(87) PCT Pub. No.: WO2008/040961
PCT Pub. Date: Apr. 10, 2008

(65) Prior Publication Data
US 2010/0292743 A1    Nov. 18, 2010

(30) Foreign Application Priority Data
Oct. 3, 2006 (GB) .................................. 0619534.1

(51) Int. Cl.
*A61B 17/17* (2006.01)
(52) U.S. Cl.
CPC .................................. *A61B 17/175* (2013.01)
(58) Field of Classification Search
CPC .......................... A61B 17/175; A61B 17/1753
USPC .......... 623/22.11, 22.12, 22.15, 20.36, 20.32
See application file for complete search history.

(56) References Cited

U.S. PATENT DOCUMENTS

| 2,416,228 | A | * | 2/1947 | Sheppard ..................... 408/105 |
| 3,330,611 | A | | 7/1967 | Heifetz |
| 3,975,858 | A | | 8/1976 | Much |
| 4,457,306 | A | | 7/1984 | Borzone |
| 4,565,191 | A | | 1/1986 | Slocum |
| 4,689,984 | A | | 9/1987 | Kellner |
| 4,706,660 | A | | 11/1987 | Petersen |

(Continued)

FOREIGN PATENT DOCUMENTS

| CN | 102038553 A | 5/2011 |
| CN | 102335742 A | 2/2012 |

(Continued)

OTHER PUBLICATIONS

Great Britain Search Report mailed Dec. 18, 2006 for GB0619534.1 filed Oct. 3, 2006 of which PCT/GB2007/003737 filed Oct. 2, 2007 claims benefit; of which US U.S. Appl. No. 12/444,143, filed Jul. 9, 2010 claims benefit.

(Continued)

*Primary Examiner* — Samuel Hanna
(74) *Attorney, Agent, or Firm* — Schwegman Lundberg & Woessner, P.A.

(57) ABSTRACT

An instrument (2) for aligning a surgical tool, the instrument (2) comprising, a body portion (4) having a tool guide (90), first and second arms (6), (8) operatively connected to the body portion (4) and adapted to engage a bone, and urging means (10), acting between the body portion (4) and the first and second arms (6), (8), for urging the first and second arms (6), (8) into engagement with a predetermined portion of a bone, thereby clamping the arms (6), (8) onto the bone and aligning the tool guide (90) with the bone.

8 Claims, 4 Drawing Sheets (56) References Cited

U.S. PATENT DOCUMENTS

| | | | |
|---|---|---|---|
| 4,719,907 A | 1/1988 | Banko et al. | |
| 4,759,350 A | 7/1988 | Dunn et al. | |
| 4,892,545 A | 1/1990 | Day et al. | |
| 4,896,663 A * | 1/1990 | Vandewalls | A61B 17/175 269/236 |
| 4,907,577 A | 3/1990 | Wu | |
| 5,006,121 A | 4/1991 | Hafeli | |
| 5,030,219 A | 7/1991 | Matsen, III et al. | |
| 5,056,351 A | 10/1991 | Stiver et al. | |
| 5,123,927 A | 6/1992 | Duncan et al. | |
| 5,194,066 A | 3/1993 | Van Zile | |
| 5,234,433 A | 8/1993 | Bert et al. | |
| 5,253,506 A | 10/1993 | Davis et al. | |
| 5,282,802 A | 2/1994 | Mahony, III | |
| 5,320,529 A | 6/1994 | Pompa | |
| 5,323,697 A | 6/1994 | Schrock | |
| 5,411,521 A | 5/1995 | Putnam et al. | |
| 5,462,550 A | 10/1995 | Dietz et al. | |
| 5,545,222 A | 8/1996 | Bonutti | |
| 5,593,411 A | 1/1997 | Stalcup et al. | |
| 5,601,565 A | 2/1997 | Huebner | |
| 5,611,802 A | 3/1997 | Samuelson et al. | |
| 5,653,714 A | 8/1997 | Dietz et al. | |
| 5,662,710 A | 9/1997 | Bonutti | |
| 5,676,668 A | 10/1997 | McCue et al. | |
| 5,683,469 A | 11/1997 | Johnson et al. | |
| 5,702,464 A | 12/1997 | Lackey et al. | |
| 5,709,689 A | 1/1998 | Ferrante et al. | |
| 5,720,752 A | 2/1998 | Elliott et al. | |
| 5,745,834 A | 4/1998 | Bampton et al. | |
| 5,766,251 A | 6/1998 | Koshino | |
| 5,776,200 A | 7/1998 | Johnson et al. | |
| 5,835,619 A | 11/1998 | Morimoto et al. | |
| 5,885,298 A | 3/1999 | Herrington et al. | |
| 5,888,219 A | 3/1999 | Bonutti | |
| 6,008,433 A | 12/1999 | Stone | |
| 6,019,767 A | 2/2000 | Howell | |
| 6,042,612 A | 3/2000 | Voydeville | |
| 6,066,175 A | 5/2000 | Henderson et al. | |
| 6,126,692 A | 10/2000 | Robie et al. | |
| 6,156,069 A * | 12/2000 | Amstutz | A61B 17/15 623/22.11 |
| 6,159,217 A | 12/2000 | Robie et al. | |
| 6,210,445 B1 | 4/2001 | Zawadzki | |
| 6,238,435 B1 | 5/2001 | Meulink et al. | |
| 6,270,529 B1 | 8/2001 | Terrill-Grisoni et al. | |
| 6,302,913 B1 | 10/2001 | Ripamonti et al. | |
| 6,310,269 B1 | 10/2001 | Friese et al. | |
| 6,322,728 B1 | 11/2001 | Brodkin et al. | |
| 6,327,491 B1 | 12/2001 | Franklin et al. | |
| 6,361,563 B2 | 3/2002 | Terrill-Grisoni et al. | |
| 6,379,388 B1 | 4/2002 | Ensign et al. | |
| 6,508,980 B1 | 1/2003 | Allen et al. | |
| 6,519,998 B2 | 2/2003 | Ertl et al. | |
| 6,551,325 B2 | 4/2003 | Neubauer et al. | |
| 6,562,073 B2 | 5/2003 | Foley | |
| 6,610,067 B2 | 8/2003 | Tallarida et al. | |
| 6,676,892 B2 | 1/2004 | Das et al. | |
| 6,916,324 B2 | 7/2005 | Sanford et al. | |
| 6,975,755 B1 | 12/2005 | Baumberg | |
| 6,993,406 B1 | 1/2006 | Cesarano, III et al. | |
| 7,001,385 B2 | 2/2006 | Bonutti | |
| 7,121,832 B2 | 10/2006 | Hsieh et al. | |
| D533,664 S | 12/2006 | Buttler et al. | |
| 7,174,282 B2 | 2/2007 | Hollister et al. | |
| 7,519,540 B2 | 4/2009 | Mayaud | |
| 7,537,664 B2 | 5/2009 | O'Neill et al. | |
| 7,603,192 B2 | 10/2009 | Martin et al. | |
| 7,747,305 B2 | 6/2010 | Dean et al. | |
| D622,854 S | 8/2010 | Otto et al. | |
| 7,789,885 B2 | 9/2010 | Metzger | |
| 7,833,245 B2 | 11/2010 | Kaes et al. | |
| 7,837,690 B2 | 11/2010 | Metzger | |
| 7,926,363 B2 | 4/2011 | Miller et al. | |
| 7,988,736 B2 | 8/2011 | May et al. | |
| 8,066,708 B2 | 11/2011 | Lang et al. | |
| 8,105,330 B2 | 1/2012 | Fitz et al. | |
| 8,122,582 B2 | 2/2012 | Burdulis, Jr. et al. | |
| 8,147,861 B2 | 4/2012 | Jones et al. | |
| 8,160,345 B2 | 4/2012 | Pavlovskaia et al. | |
| 8,192,495 B2 | 6/2012 | Simpson et al. | |
| 8,200,355 B2 | 6/2012 | Lee et al. | |
| 8,221,430 B2 | 7/2012 | Park et al. | |
| 8,246,680 B2 | 8/2012 | Betz et al. | |
| 8,260,589 B1 | 9/2012 | Kumar | |
| 8,268,099 B2 | 9/2012 | O'Neill et al. | |
| 8,268,100 B2 | 9/2012 | O'Neill et al. | |
| D669,176 S | 10/2012 | Frey | |
| 8,313,491 B2 | 11/2012 | Green, II et al. | |
| D672,038 S | 12/2012 | Frey | |
| 8,337,503 B2 | 12/2012 | Lian | |
| 8,355,773 B2 | 1/2013 | Leitner et al. | |
| 8,372,078 B2 | 2/2013 | Collazo | |
| 8,377,066 B2 | 2/2013 | Katrana et al. | |
| 8,388,690 B2 | 3/2013 | Singhatat et al. | |
| 8,398,646 B2 | 3/2013 | Metzger et al. | |
| 8,407,067 B2 | 3/2013 | Uthgenannt et al. | |
| 8,414,594 B2 | 4/2013 | Berger et al. | |
| 8,419,741 B2 | 4/2013 | Carignan et al. | |
| 8,425,522 B2 | 4/2013 | Bonutti | |
| 8,430,882 B2 | 4/2013 | Lowry et al. | |
| 8,430,931 B2 | 4/2013 | Acker et al. | |
| 8,439,675 B2 | 5/2013 | De Moyer | |
| 8,439,925 B2 | 5/2013 | Marino et al. | |
| 8,444,564 B2 | 5/2013 | Mahfouz et al. | |
| 8,444,651 B2 | 5/2013 | Kunz et al. | |
| 8,457,930 B2 | 6/2013 | Schroeder | |
| 8,460,302 B2 | 6/2013 | Park et al. | |
| 8,469,961 B2 | 6/2013 | Alleyne et al. | |
| 8,473,305 B2 | 6/2013 | Belcher et al. | |
| 8,486,150 B2 | 7/2013 | White et al. | |
| 8,500,740 B2 | 8/2013 | Bojarski et al. | |
| 8,532,361 B2 | 9/2013 | Pavlovskaia et al. | |
| 8,532,806 B1 | 9/2013 | Masson | |
| 8,532,807 B2 | 9/2013 | Metzger | |
| 8,535,387 B2 | 9/2013 | Meridew et al. | |
| 8,543,234 B2 | 9/2013 | Gao | |
| 8,545,508 B2 | 10/2013 | Collazo | |
| 8,568,487 B2 | 10/2013 | Witt et al. | |
| 8,591,516 B2 | 11/2013 | Metzger et al. | |
| 8,597,365 B2 | 12/2013 | Meridew | |
| 8,603,180 B2 | 12/2013 | White et al. | |
| 8,608,748 B2 | 12/2013 | Metzger et al. | |
| 8,608,749 B2 | 12/2013 | Meridew et al. | |
| 8,617,170 B2 | 12/2013 | Ashby et al. | |
| 8,617,174 B2 | 12/2013 | Axelson, Jr. et al. | |
| 8,617,175 B2 | 12/2013 | Park et al. | |
| 8,632,547 B2 | 1/2014 | Maxson et al. | |
| 8,652,142 B2 | 2/2014 | Geissler | |
| 8,668,700 B2 | 3/2014 | Catanzarite et al. | |
| 8,702,712 B2 | 4/2014 | Jordan et al. | |
| 8,702,715 B2 | 4/2014 | Ammann et al. | |
| 8,706,285 B2 | 4/2014 | Narainasamy et al. | |
| 8,715,289 B2 | 5/2014 | Smith | |
| 8,728,387 B2 | 5/2014 | Jones et al. | |
| 8,735,773 B2 | 5/2014 | Lang | |
| 8,764,760 B2 | 7/2014 | Metzger et al. | |
| 8,775,133 B2 | 7/2014 | Schroeder | |
| 8,777,875 B2 | 7/2014 | Park | |
| 8,828,016 B2 | 9/2014 | Major et al. | |
| 8,828,087 B2 | 9/2014 | Stone et al. | |
| 8,828,089 B1 | 9/2014 | Perez et al. | |
| 8,834,568 B2 | 9/2014 | Shapiro | |
| 8,858,561 B2 | 10/2014 | White et al. | |
| 8,864,769 B2 | 10/2014 | Stone et al. | |
| 8,900,244 B2 | 12/2014 | Meridew et al. | |
| 8,903,530 B2 | 12/2014 | Metzger | |
| 8,956,364 B2 | 2/2015 | Catanzarite et al. | |
| 8,979,936 B2 | 3/2015 | White et al. | |
| 9,005,297 B2 | 4/2015 | Katrana | |
| 2001/0021876 A1 | 9/2001 | Terrill-Grisoni et al. | |
| 2002/0186818 A1 | 12/2002 | Arnaud et al. | |
| 2002/0193797 A1 | 12/2002 | Johnson et al. | |
| 2002/0198528 A1 | 12/2002 | Engh et al. | |

(56) References Cited

U.S. PATENT DOCUMENTS

| | | |
|---|---|---|
| 2002/0198531 A1 | 12/2002 | Millard et al. |
| 2004/0054416 A1 | 3/2004 | Wyss et al. |
| 2004/0122436 A1 | 6/2004 | Grimm |
| 2004/0193169 A1 | 9/2004 | Schon et al. |
| 2005/0113841 A1 | 5/2005 | Sheldon et al. |
| 2005/0209597 A1* | 9/2005 | Long et al. ............ 606/86 |
| 2005/0209605 A1 | 9/2005 | Grimm et al. |
| 2005/0222571 A1 | 10/2005 | Ryan |
| 2005/0234465 A1 | 10/2005 | McCombs et al. |
| 2005/0245934 A1 | 11/2005 | Tuke et al. |
| 2005/0245936 A1 | 11/2005 | Tuke et al. |
| 2006/0105011 A1 | 5/2006 | Sun et al. |
| 2006/0122618 A1 | 6/2006 | Claypool et al. |
| 2006/0147332 A1 | 7/2006 | Jones et al. |
| 2006/0161165 A1 | 7/2006 | Swanson |
| 2006/0192319 A1* | 8/2006 | Solar ............ 264/271.1 |
| 2006/0271058 A1 | 11/2006 | Ashton et al. |
| 2006/0287891 A1 | 12/2006 | Grasso et al. |
| 2007/0016008 A1 | 1/2007 | Schoenefeld |
| 2007/0039205 A1 | 2/2007 | Erb et al. |
| 2007/0043582 A1 | 2/2007 | Peveto et al. |
| 2007/0073133 A1 | 3/2007 | Schoenefeld |
| 2007/0073136 A1 | 3/2007 | Metzger |
| 2007/0106299 A1 | 5/2007 | Manspeizer |
| 2007/0129809 A1 | 6/2007 | Meridew et al. |
| 2007/0142914 A1 | 6/2007 | Jones et al. |
| 2007/0198022 A1 | 8/2007 | Lang et al. |
| 2007/0233136 A1 | 10/2007 | Wozencroft |
| 2007/0276400 A1 | 11/2007 | Moore et al. |
| 2008/0094396 A1 | 4/2008 | Sabczynsdi et al. |
| 2008/0147074 A1 | 6/2008 | Ammann et al. |
| 2008/0269596 A1 | 10/2008 | Revie et al. |
| 2009/0024169 A1 | 1/2009 | Triplett et al. |
| 2009/0048618 A1 | 2/2009 | Harrison et al. |
| 2009/0076555 A1 | 3/2009 | Lowry et al. |
| 2009/0088759 A1 | 4/2009 | Aram et al. |
| 2009/0116621 A1 | 5/2009 | Yuan et al. |
| 2009/0250413 A1 | 10/2009 | Hoeppner |
| 2009/0287309 A1 | 11/2009 | Walch et al. |
| 2010/0016984 A1 | 1/2010 | Trabish |
| 2010/0036404 A1 | 2/2010 | Yi et al. |
| 2010/0082067 A1 | 4/2010 | Kondrashov |
| 2010/0160919 A1 | 6/2010 | Axelson, Jr. et al. |
| 2010/0168866 A1 | 7/2010 | Shih |
| 2010/0198067 A1 | 8/2010 | Mahfouz et al. |
| 2010/0217399 A1 | 8/2010 | Groh |
| 2010/0256649 A1 | 10/2010 | Capsal et al. |
| 2010/0274253 A1 | 10/2010 | Ure |
| 2010/0291401 A1 | 11/2010 | Medina et al. |
| 2010/0298894 A1 | 11/2010 | Bojarski et al. |
| 2011/0008754 A1 | 1/2011 | Bassett et al. |
| 2011/0014081 A1 | 1/2011 | Jones et al. |
| 2011/0016690 A1 | 1/2011 | Narainasamy et al. |
| 2011/0022174 A1 | 1/2011 | Holdstein et al. |
| 2011/0029088 A1 | 2/2011 | Rauscher et al. |
| 2011/0071581 A1 | 3/2011 | Lang et al. |
| 2011/0071802 A1 | 3/2011 | Bojarski et al. |
| 2011/0087332 A1 | 4/2011 | Bojarski et al. |
| 2011/0106093 A1 | 5/2011 | Romano et al. |
| 2011/0125284 A1 | 5/2011 | Gabbrielli et al. |
| 2011/0177590 A1 | 7/2011 | Clyne et al. |
| 2011/0238071 A1 | 9/2011 | Fernandez-Scoma |
| 2011/0245835 A1 | 10/2011 | Dodds et al. |
| 2011/0276145 A1 | 11/2011 | Carignan et al. |
| 2011/0282473 A1 | 11/2011 | Pavlovskaia et al. |
| 2011/0295887 A1 | 12/2011 | Palmese et al. |
| 2011/0313424 A1 | 12/2011 | Bono et al. |
| 2011/0319745 A1 | 12/2011 | Frey |
| 2012/0029345 A1 | 2/2012 | Mahfouz et al. |
| 2012/0029520 A1 | 2/2012 | Lang et al. |
| 2012/0041445 A1 | 2/2012 | Roose et al. |
| 2012/0041564 A1 | 2/2012 | Landon |
| 2012/0078254 A1 | 3/2012 | Ashby et al. |
| 2012/0078258 A1 | 3/2012 | Lo et al. |
| 2012/0116203 A1 | 5/2012 | Vancraen et al. |
| 2012/0123422 A1 | 5/2012 | Agnihotri et al. |
| 2012/0150242 A1 | 6/2012 | Mannion |
| 2012/0158002 A1 | 6/2012 | Carignan et al. |
| 2012/0165954 A1 | 6/2012 | Nimal |
| 2012/0192401 A1 | 8/2012 | Pavlovskaia et al. |
| 2012/0215310 A1 | 8/2012 | Sharp et al. |
| 2012/0245587 A1 | 9/2012 | Fang et al. |
| 2012/0259335 A1 | 10/2012 | Scifert et al. |
| 2012/0271131 A1 | 10/2012 | Kling et al. |
| 2012/0310364 A1 | 12/2012 | Li et al. |
| 2012/0323282 A1 | 12/2012 | Brianza et al. |
| 2012/0323323 A1 | 12/2012 | Vargas et al. |
| 2013/0018483 A1 | 1/2013 | Li et al. |
| 2013/0046310 A1 | 2/2013 | Ranawat et al. |
| 2013/0053854 A1 | 2/2013 | Schoenefeld et al. |
| 2013/0056912 A1 | 3/2013 | O'Neill et al. |
| 2013/0060253 A1 | 3/2013 | Couture et al. |
| 2013/0072940 A1 | 3/2013 | Dawood et al. |
| 2013/0085500 A1 | 4/2013 | Meridew et al. |
| 2013/0085590 A1 | 4/2013 | Bryan et al. |
| 2013/0123850 A1 | 5/2013 | Schoenefeld et al. |
| 2013/0131681 A1 | 5/2013 | Katrana et al. |
| 2013/0144392 A1 | 6/2013 | Hughes |
| 2013/0197528 A1 | 8/2013 | Zakaria et al. |
| 2013/0197529 A1 | 8/2013 | Metzger et al. |
| 2013/0197687 A1 | 8/2013 | Pavlovskaia et al. |
| 2013/0218163 A1 | 8/2013 | Frey |
| 2013/0245631 A1 | 9/2013 | Bettenga |
| 2013/0245801 A1 | 9/2013 | Schroeder |
| 2013/0261503 A1 | 10/2013 | Sherman et al. |
| 2013/0264749 A1 | 10/2013 | Jones et al. |
| 2013/0268085 A1 | 10/2013 | Dong et al. |
| 2013/0289730 A1 | 10/2013 | Gabriel et al. |
| 2013/0317511 A1 | 11/2013 | Bojarski et al. |
| 2013/0326878 A1 | 12/2013 | Boehm et al. |
| 2013/0338673 A1 | 12/2013 | Keppler |
| 2014/0005672 A1 | 1/2014 | Edwards et al. |
| 2014/0012266 A1 | 1/2014 | Bonin, Jr. et al. |
| 2014/0052270 A1 | 2/2014 | Witt et al. |
| 2014/0066937 A1 | 3/2014 | Wiebe, Iii et al. |
| 2014/0081275 A1 | 3/2014 | Metzger et al. |
| 2014/0081659 A1 | 3/2014 | Nawana et al. |
| 2014/0088724 A1 | 3/2014 | Meridew |
| 2014/0094816 A1 | 4/2014 | White et al. |
| 2014/0100578 A1 | 4/2014 | Metzger et al. |
| 2014/0107651 A1 | 4/2014 | Meridew et al. |
| 2014/0107654 A1 | 4/2014 | Kehres et al. |
| 2014/0107715 A1 | 4/2014 | Heilman et al. |
| 2014/0127211 A1 | 5/2014 | Geles et al. |
| 2014/0135775 A1 | 5/2014 | Maxson et al. |
| 2014/0163564 A1 | 6/2014 | Bollinger |
| 2014/0163565 A1 | 6/2014 | Bollinger |
| 2014/0172116 A1 | 6/2014 | Maxson et al. |
| 2014/0188119 A1 | 7/2014 | Catanzarite et al. |
| 2014/0222157 A1 | 8/2014 | Al Hares et al. |
| 2014/0243833 A1 | 8/2014 | Smith |
| 2014/0257304 A1 | 9/2014 | Eash |
| 2014/0257508 A1 | 9/2014 | Bojarski et al. |
| 2014/0276854 A1 | 9/2014 | Schoenefeld et al. |
| 2014/0276856 A1 | 9/2014 | Schoenefeld |
| 2014/0276870 A1 | 9/2014 | Eash |
| 2014/0276873 A1 | 9/2014 | Meridew et al. |
| 2014/0303938 A1 | 10/2014 | Schoenefeld et al. |
| 2014/0303990 A1 | 10/2014 | Schoenefeld et al. |
| 2014/0309644 A1 | 10/2014 | Metzger et al. |
| 2014/0324058 A1 | 10/2014 | Metzger et al. |
| 2014/0378979 A1 | 12/2014 | Stone et al. |
| 2015/0088293 A1 | 3/2015 | Metzger |

FOREIGN PATENT DOCUMENTS

| | | |
|---|---|---|
| DE | 10341187 A1 | 3/2005 |
| EP | 0255797 A1 | 2/1988 |
| EP | 1 588 669 A | 10/2005 |
| EP | 1588669 A | 10/2005 |
| EP | 1634551 A2 | 3/2006 |
| EP | 2502582 A1 | 9/2012 |
| EP | 2709568 A1 | 3/2014 |
| FR | 2979817 A1 | 3/2013 |

(56) References Cited

FOREIGN PATENT DOCUMENTS

| GB | 2423021 | | 8/2006 |
|----|---------|---|--------|
| JP | 6-233790 | A | 8/1994 |
| JP | 2000245758 | A | 9/2000 |
| JP | 2005-218861 | A | 8/2005 |
| JP | 2009514612 | A | 4/2009 |
| RU | 2218242 | C2 | 12/2003 |
| WO | WO-2005/051209 | A | 6/2005 |
| WO | WO-2005051209 | A | 6/2005 |
| WO | WO-2005051233 | A2 | 6/2005 |
| WO | WO-2006134345 | A1 | 12/2006 |
| WO | WO2008040961 | A1 | 4/2008 |
| WO | WO-2010124164 | A1 | 10/2010 |
| WO | WO-2010129870 | A1 | 11/2010 |
| WO | WO-2010150223 | A1 | 12/2010 |
| WO | WO-2011080260 | A1 | 7/2011 |
| WO | WO-2011117644 | A2 | 9/2011 |
| WO | WO-2013170872 | A1 | 11/2013 |
| WO | WO-2014019712 | A1 | 2/2014 |

OTHER PUBLICATIONS

International Preliminary Report on Patentability issued Apr. 7, 2009 for PCT/GB2007/003737 filed Oct. 2, 2007 of which U.S. Appl. No. 12/444,143 claims benefit.
International Search Report and Written Opinion mailed Jan. 25, 2008 for PCT/GB2007/003737 filed Oct. 2, 2007 of which U.S. Appl. No. 12/444,143 claims benefit.
International Preliminary Report on Patentability and Written Opinion mailed Jan. 3, 2014 for PCT/US2012/042081 claiming benefit of U.S. Appl. No. 13/493,509, filed Jun. 11, 2012.
International Preliminary Report on Patentability and Written Opinion mailed Nov. 28, 2013 for PCT/US2012/038351 claiming benefit of U.S. Appl. No. 13/111,007, filed May 19, 2011.
International Preliminary Report on Patentability and Written Opinion mailed Apr. 24, 2014 for PCT/US2012/059189 claiming benefit of U.S. Appl. No. 13/597,478 filed Aug. 29, 2012.
International Preliminary Report on Patentability and Written Opinion mailed Mar. 13, 2014 for PCT/US2012/052853 claiming benefit of U.S. Appl. No. 13/221,968, filed Aug. 31, 2011.
International Search Report and Written Opinion mailed Apr. 14, 2014 for PCT/US2013/067505 claiming benefit of U.S. Appl. No. 13/718,129, filed Dec. 18, 2012.
International Search Report and Written Opinion mailed Oct. 14, 2013 for PCT/US2013/057097 claiming benefit of U.S. Appl. No. 13/597,478, filed Aug. 29, 2012.
Invitation to Pay Additional Fees mailed Feb. 6, 2014 for PCT/US2013/067505, which claims benefit of U.S. Appl. No. 13/718,129, filed Dec. 18, 2012.
Signature™ Personalized Patient Care, Surgical Technique Addendum Vangaurd® Complete Knee System, Biomet® Orthopedics Brochure, (2011), p. 1-32.
"Is Subchondroplasty® Right for Me?" Retrieved from <http://www.subchondroplasty.com/about subchondroplasty/is_subchondroplasty_right_for_>. . . Jul. 1, 2013. 1 sheet.
"Subchondroplasty," Retrieved from <http://www.subchondroplasty.com/>. Jul. 1, 2013. 1 sheet.
Deakon, Timothy, Md, Posterior Cruciate Ligament Reconstruction Technique Using the Modular ACL/PCL Guide Rationale and Surgical Technique, Arthrotek® , a Biomet Company. (2003). (6 pages).
International Preliminary Report on Patentability and Written Opinion mailed May 8, 2014 for PCT/US2012/060842 claiming benefit of U.S. Appl. No. 13/653, 868 filed Oct. 17, 2012.
International Preliminary Report on Patentability and Written Opinion mailed May 8, 2014 for PCT/US2012/060848 claiming benefit of U.S. Appl. No. 13/653,878 filed Oct. 17, 2012.
International Preliminary Report on Patentability and Written Opinion mailed May 8, 2014 for PCT/US2012/060853 claiming benefit of U.S. Appl. No. 13/653,886 filed Oct. 17, 2012.
International Preliminary Report on Patentability and Written Opinion mailed May 8, 2014 for PCT/US2012/060854 claiming benefit of U.S. Appl. No. 13/653,893 filed Oct. 17, 2012.
International Search Report and Written Opinion mailed Jun. 24, 2014 for PCT/US2014/022000 claiming benefit of U.S. Appl. No. 13/889,869 filed May 8, 2013.
International Search Report and Written Opinion mailed May 23, 2014 for PCT/US2013/074288 claiming benefit of U.S. Appl. No. 13/790,770, filed Mar. 8, 2013, which priority is also claimed of U.S. Appl. No. 13/711,306, filed Dec. 11, 2012.
What is Subchondroplasty, Retrieved from <http://www.subchondroplasty.com/about_subchondroplasty/what_is_subchondroplasty. >, Jul. 1, 2013. 2 sheets.
International Preliminary Report on Patentability Report and Written Opinion mailed Sep. 4, 2014 for PCT/US2013/026875 claiming benefit of U.S. Appl. No. 13/400,652, filed Feb. 21, 2012.
International Search Report and Written Opinion mailed Jul. 10, 2014 for PCT/US2014/023655 claiming benefit of U.S. Appl. No. 13/800,369 filed Mar. 13, 2013.
European Communication Pursuant to Article 94(3) EPC mailed Jan. 22, 2015 for PCT/US2007/013223 filed Jun. 5, 2007, which claims benefit of U.S. Appl. No. 60/812,694, filed Jun. 9, 2006 and U.S. Appl. No. 11/756,057, filed May 31, 2007.
European Communication Pursuant to Article 94(3) EPC mailed Feb. 4, 2015 for PCT/US2010/024584 filed Feb. 18, 2010, which claims benefit of U.S. Appl. No. 12/389,901, filed Feb. 20, 2009.
European Communication Pursuant to Article 94(3) EPC mailed Feb. 10, 2015 for PCT/US2009/039507 filed Apr. 3, 2009, which claims benefit of U.S. Appl. No. 12/103,824, filed Apr. 16, 2008.
European Communication Pursuant to Article 94(3) EPC mailed Nov. 24, 2014 for PCT/US2012/038351 which claims benefit of U.S. Appl. No. 13/111,007, filed May 19, 2011.
Farr, J., Cole, B. , Kercher, J., Batty, L. And Bajaj, S., Anteromedial Tibial Tubercle Osteotomy (Fulkerson Osteotomy). Re-print from V. Sanchis-Alfonso (ed), Anterior Knee Pain and patellar Instability, DOI: 10.1007/978-0-85729-507-1_40,© Springer-Verlag London Limited 2011.(9 pages).
Farr, J., Fulkerson, J. Surgical Technique for Anteromedialization of the Tibial Tubercle with the Tracker™ AMZ Guide System. Sports Medicine and Arthroscopy Review, vol. 2, No. 3, 1994. (12 pages).
International Preliminary Report on Patentability and Written Opinion mailed on Mar. 12, 2015 for PCT/US2013/057097 claiming benefit of U.S. Appl. No. 13/597,478, filed on Aug. 29, 2012.
Japanese Office Action mailed on Apr. 7, 2015 for PCT/US2012/038351 filed May 17, 2012 claiming benefit of U.S. Appl. No. 13/111,007, filed on May 19, 2011.
Patent Examiniation Report No. 1 mailed Feb. 16, 2015 for PCT/US2013/026875 filed Feb. 20, 2013, which claims benefit of U.S. Appl. No. 13/400,652, filed Feb. 21, 2012.
Signature™ Hip Technology Personalized Patient Care brochure. Biomet® Orthopedics. (2013) (8 pages).
Signature™ Personalized Patient Care. Surgical Technique Acetabular Guide System brochure. Biomet® Orthopedics. (2013) pp. 1-13.
International Preliminary Report on Patentability mailed Sep. 6, 2013 for PCT/US2012/026356 claiming benefit of U.S. Application No. 13/041,883 filed Mar. 7, 2011.
International Search Report and Written Opinion for PCT/US2013/026875 mailed Jun. 7, 2013, claiming benefit of U.S. Appl. No. 13/400,652, filed Feb. 21, 2012.
International Search Report and Written Opinion mailed Oct. 14, 2013 for PCT/US2013/057097 claiming benefit of U.S. Appl. No. 13/597,478 filed Aug. 29, 2012.
"European Application Serial No. 07823994.4, Decision to Grant mailed Feb. 4, 2016", 2 pgs.
"European Application Serial No. 07823994.4, Examination Notification Art. 94(3) mailed Feb. 25, 2014", 4 pgs.
"European Application Serial No. 07823994.4, Examination Notification Art. 94(3) mailed May 8, 2012", 5 pgs.
"European Application Serial No. 07823994.4, Office Action mailed Mar. 23, 2015", 20 pgs.
"European Application Serial No. 07823994.4, Office Action mailed Aug. 19, 2015", 20 pgs.

(56) References Cited

OTHER PUBLICATIONS

"European Application Serial No. 07823994.4, Response filed Jul. 3, 2014 to Examination Notification Art. 94(3) mailed Feb. 25, 2014", 6 pgs.

"European Application Serial No. 07823994.4, Response filed Nov. 6, 2012 to Examination Notification Art. 94(3) mailed May 8, 2012", 14 pgs.

\* cited by examiner

SURGICAL INSTRUMENT

This invention relates to a surgical instrument and particularly, but not exclusively, relates to an instrument having a tool guide and a clamping arrangement, the clamping arrangement clamping the instrument to a bone, and at the same time aligning the tool guide with the bone.

BACKGROUND

During all types of joint replacement surgery, and in many other surgical procedures, it is necessary to make specific cuts or to drill holes into specific areas of bone. Both the point and angle of entry of the cut or drill hole is important. This is particularly so in the case, for example, of femoral head resurfacing, where it is necessary to drill a pilot hole that passes through the centre of the femoral neck at a specific angle with respect both to the epicondylar axis and the femoral shaft axis. Guide tools exist to aid surgeons in the placement of bone cuts and guide holes. Such tools are often difficult and time consuming to operate, and are inaccurate. Many of the tools of the prior art are also bulky, requiring the removal or displacement of large areas of soft tissue in order to be used.

Use of conventional tool guides generally involves at least the steps of attaching the guide, referencing the position of the guide from an anatomical feature, and adjusting the position of the guide to correspond to the optimal position indicated in the referencing step. Several iterations of referencing and adjustment may be required to achieve the correct position and orientation of the guide.

STATEMENTS OF INVENTION

According to a first aspect of the present invention, there is provided an instrument for aligning a surgical tool, the instrument comprising, a body portion having a tool guide, first and second arms operatively connected to the body portion and adapted to engage a bone, and urging means, acting between the body portion and the first and second arms, for urging the first and second arms into engagement with a predetermined portion of a bone, thereby clamping the arms onto the bone and aligning the tool guide with the bone.

The first and second arms may terminate in first and second jaws. The first jaw may be curved and the second jaw may be bifurcated and may have at least two distinct jaw elements. As the instrument contacts the bone in at least three distinct points or areas, the instrument is held in a very stable manner relative to the bone.

The first and second arms may be pivotally connected to the body portion. Alternatively, the first and second arms may be connected to the body portion by means of a linkage which constrains the arms to translate laterally of the body portion towards and away from one another. The linkage may be a quadrilateral linkage. The advantage of constraining the arms to translate laterally is that the angle of the arms relative to a longitudinal axis of the body portion does not change irrespective of the diameter of the bone to be clamped. This enhances the accuracy of referencing and hence the alignment of the tool guide compared to an instrument having pivoting arms, irrespective of the size of the patient.

The first and second arms may be disposed on opposite sides of the body portion. Additional arms may also be provided. For example, three arms may be provided spaced equidistantly around the circumference of the body portion.

The urging means may engage the body portion via a threaded connection, and the urging means may be a nut. The nut may comprise a tapering engagement surface, configured to engage the first and second arms directly.

The body portion may comprise a post having projecting tabs that extend from the base of the post. The first and second arms may be mounted in opposed recesses formed in the projecting tabs. Each arm may be pivotably connected to one of the tabs by means of a pinned joint.

Each arm may be connected to the body portion at an intermediate position along its length.

The tool guide may be provided with a plurality of tool guiding openings. At least one of the tool guiding openings may be differently aligned to the or each other tool guiding openings, so that when the first and second arms are clamped to the bone, the said tool guiding opening is aligned with a different part of the bone from the or each other tool guiding opening.

The tool guiding openings may comprise bores having longitudinal axes at least some of which converge at a point a predetermined distance proximal of the body portion. The longitudinal axes of some of the bores may converge at a different point from the longitudinal axes of some others of the bores.

The provision of a plurality of guide holes or bores enables the surgeon to select an appropriate bore which might compensate for minor misalignment of the instrument. Furthermore, having groups of bores aligned, such that their longitudinal axes intersect at specific points, further increases the options that the surgeon has in selecting an appropriate bore to accommodate minor misalignment or variations in patient anatomy.

According to a second aspect of the present invention, there is provided an instrument for aligning a surgical tool, the instrument comprising a body portion, at least two arms pivotably connected to the body portion and a nut which engages a thread formed on the body portion, the nut engaging the arms as it is threaded onto the body portion in use, thereby forcing the free ends of the arms together to clamp a bone.

According to a third aspect of the present invention, there is provided an instrument for aligning a surgical tool, the instrument comprising a body portion, means for clamping the body portion to a bone, and a tool guide having a plurality of tool guide bores, longitudinal axes of some of the bores converging at a different point from longitudinal axes of others of the bores.

The instrument my be used in a method of aligning a tool guide, the method comprising the steps of:
a placing the arms of the instrument about a predetermined portion of a bone; and
b operating the urging means to force the arms to clamp the bone, thereby aligning the tool guide with the bone.

The present invention represents a considerable advance over prior art devices, since simply by operating the urging means to force the arms to clamp a predetermined portion of the bone, the tool guide is automatically aligned with the bone. This is achieved because the arms of the instrument reference on a predetermined portion of the bone which has a known orientation relative to the part of the bone which is to be drilled, cut of otherwise worked. The automatic alignment provided by the device means that no additional visual checks of the alignment of the device are required, thereby speeding up the surgical procedure. Furthermore, the level of skill and experience required in the surgeon using the instrument is reduced, whilst the accuracy of the surgery is increased. The instrument is also adaptable to different sizes of bone, so that a single instrument can be used on many patients.

BRIEF DESCRIPTION OF THE DRAWINGS

For a better understanding of the present invention, and to show more clearly how it may be carried into effect, reference will now be made, by way of example, to the accompanying drawings, in which: —

DETAILED DESCRIPTION OF PREFERRED EMBODIMENTS

Figure 1:
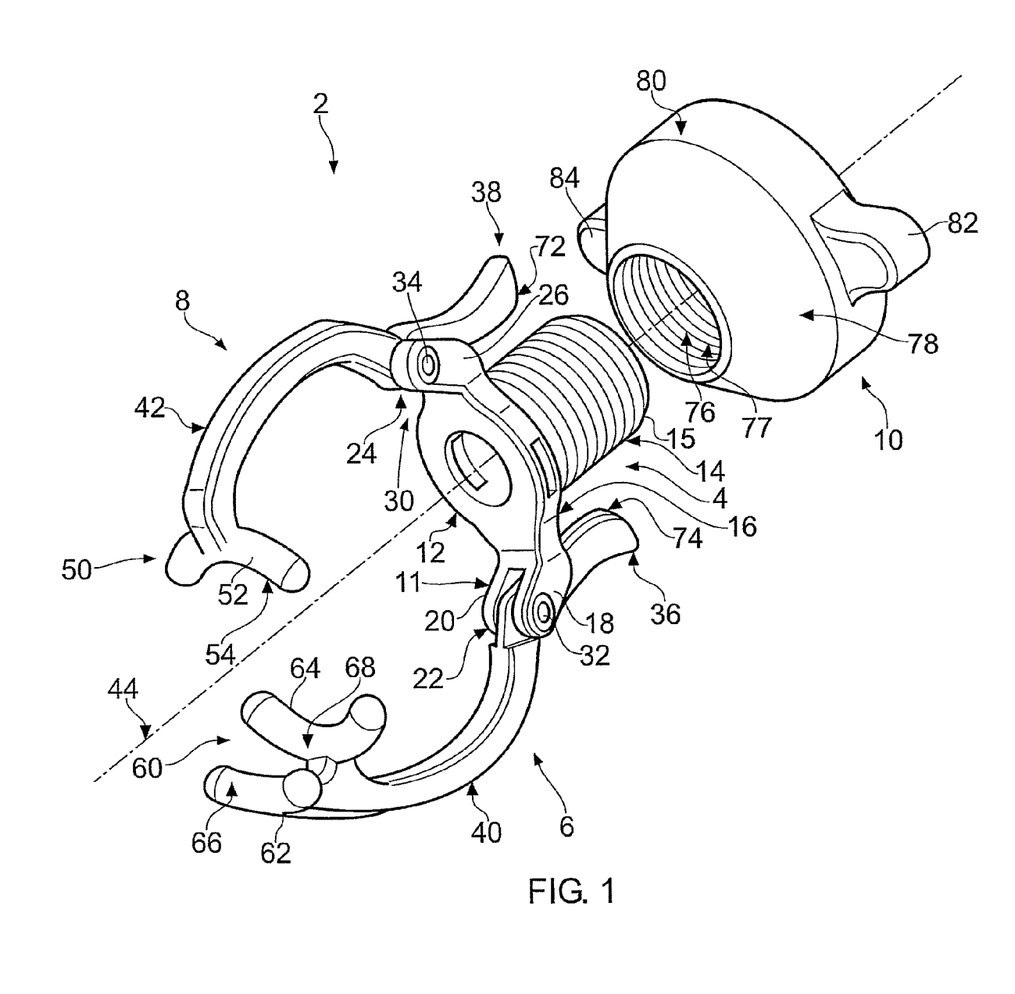
FIG. 1 is an exploded perspective view of a surgical instrument.

With reference to FIG. 1, a surgical instrument 2 comprises a body portion 4, a pair of opposed first and second arms 6, 8 pivotally connected to the body portion 4, and a nut 10 mountable on the body portion 4. The body portion 4 comprises an annular flange 12 and a post 14 that carries an external thread 15.

In this specification, the terms "distal" and "distally" mean towards the threaded end of the surgical instrument 2, and the terms "proximal" and "proximally" mean towards the opposite end of the surgical instrument 2.

The post 14 projects substantially perpendicularly from a distal surface 16 of the flange 12. A first tab 11 projects from a first (or inferior) side of the flange 12 and is bifurcated. A recess 22 is defined between substantially parallel forks 18, 20 of the first bifurcated tab 11. A second bifurcated tab 30 projects from an opposite (or superior) side of the flange 12. A second recess 24 is defined between substantially parallel forks 26, 28 of the second bifurcated tab 30.

The arms 6, 8 are mounted on the tabs 11 and 30 for pivotal motion relative to the flange 12 and post 14. The arm 6 is mounted between the forks 18, 20 on a pin 32 which extends through the forks 18, 20, and the arm 8 is mounted between the forks 26, 28 on a pin 34 which extends through the forks 26, 28. Each arm 6, 8 includes a cylindrical bore (not shown) extending across the width of the arm 6, 8, at an intermediate position along its length, through which the corresponding pin 32, 34 passes.

Other means of pivotable connections are contemplated, such as replacing the pins 32, 34 with set screws, rivets, or nut and bolt arrangements. In an alternative embodiment, not illustrated, the arms 6, 8 are connected to the body portion 4 by a quadrilateral linkage so that the arms 6, 8 move laterally of the body portion 4, rather than pivoting about the tabs 11, 30.

Each arm 6, 8 extends both proximally and distally of its respective bore such that, when mounted in the recesses 22, 24, each arm comprises a referencing portion 40, 42, that extends proximally of the flange 12, and an engaging portion 36, 38, that extends distally of the flange 12. Each arm 6, 8 is substantially "S" shaped, and is mounted in its corresponding recess 22, 24 such that the engaging portion 36, 38 is directed away form a central axis 44 of the post 14 and the referencing portion 40, 42 is directed towards the central axis 44 of the post 14.

The referencing portion 42 of the arm 8 mounted in the second recess 24 (the superior arm) terminates at its free end in a jaw 50. The jaw 50 comprises a single jaw element 52 that extends arcuately so as to define an internal, bone receiving surface 54. The referencing portion 40 of the arm 6 mounted in the first recess 22 (the inferior arm) terminates at its free end in a jaw 60. The jaw 60 is bifurcated, comprising two jaw elements 62, 64 that each extend arcuately so as to define internal, bone receiving surfaces 66, 68.

The engagement portions 36, 38 of the arms 6, 8 define opposed curved cam surfaces 72, 74 that cooperate with an annular engagement surface formed on the nut 10.

The nut 10 comprises a bore 76 having an internal thread 77. The thread 77 cooperates with the external thread 15 formed on the post 4. The nut 10 has a frustoconical engagement surface 78 that tapers outwardly from the rim of the bore 76 to a cylindrical gripping surface 80. Projections 82, 84 are integrally formed with the cylindrical gripping surface 80 to facilitate rotation of the nut 10. Alternatively, the cylindrical gripping surface 80 may be knurled, or otherwise adapted to facilitate turning by hand. In an embodiment not illustrated, the nut may be shaped to facilitate turning using a tool.

Figure 2:
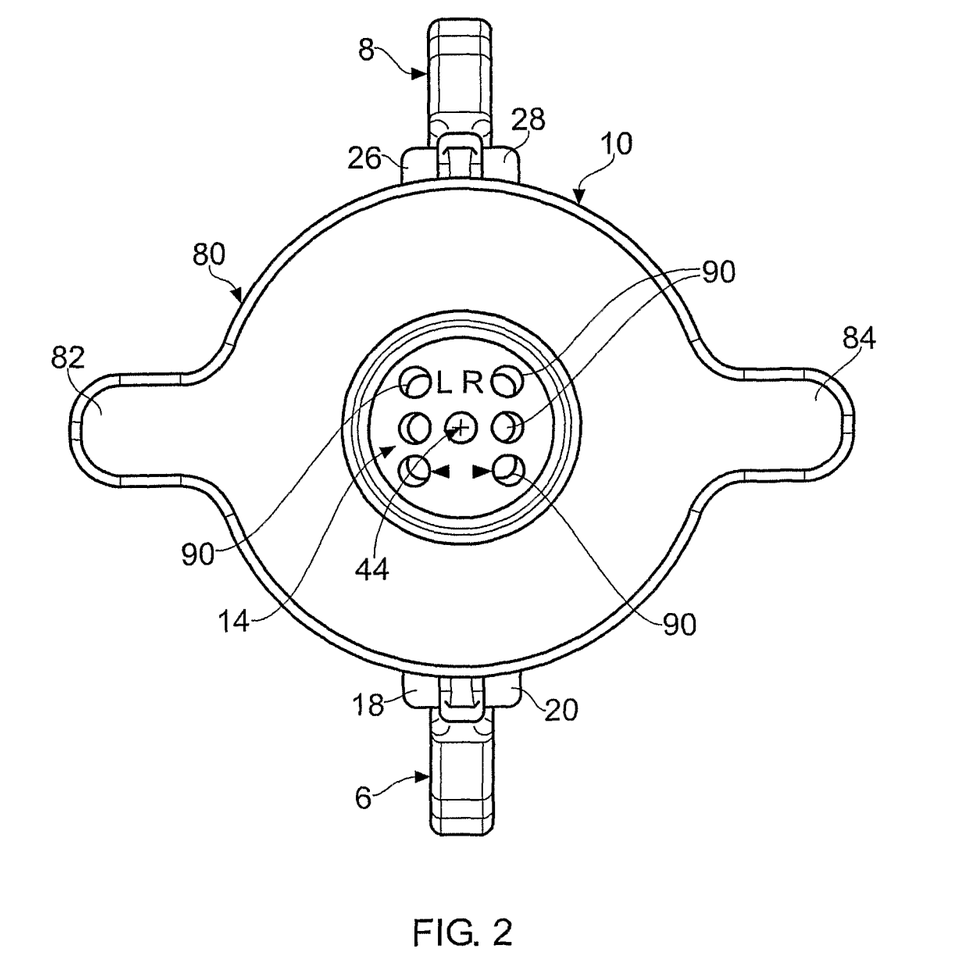
FIG. 2 is a plan view of the instrument of FIG. 1.

With reference to FIG. 2, the post 14 comprises a series of guide bores 90 extending from a distal surface of the post 14. The bores 90 are open, allowing communication from a distal to a proximal end of the body portion 4. The post 14 may be hollow, in which case the flange 12 includes a corresponding opening and the bores 90 extend through the distal end wall of the post 14. Alternatively, the post 14 may be solid, in which case the bores 90 extend through the length of the post 14 and the thickness of the flange 12. At least one bore 90 is positioned such that the axis of the bore 90 coincides with the longitudinal axis 44 of the post 14. The bores 90 are orientated such that the longitudinal axes of the bores 90 converge on predetermined points which are predetermined distances proximal of the body portion 4.

The instrument 2 is particularly suited for use in surgical procedures involving the hip and shoulder.

Figure 3:
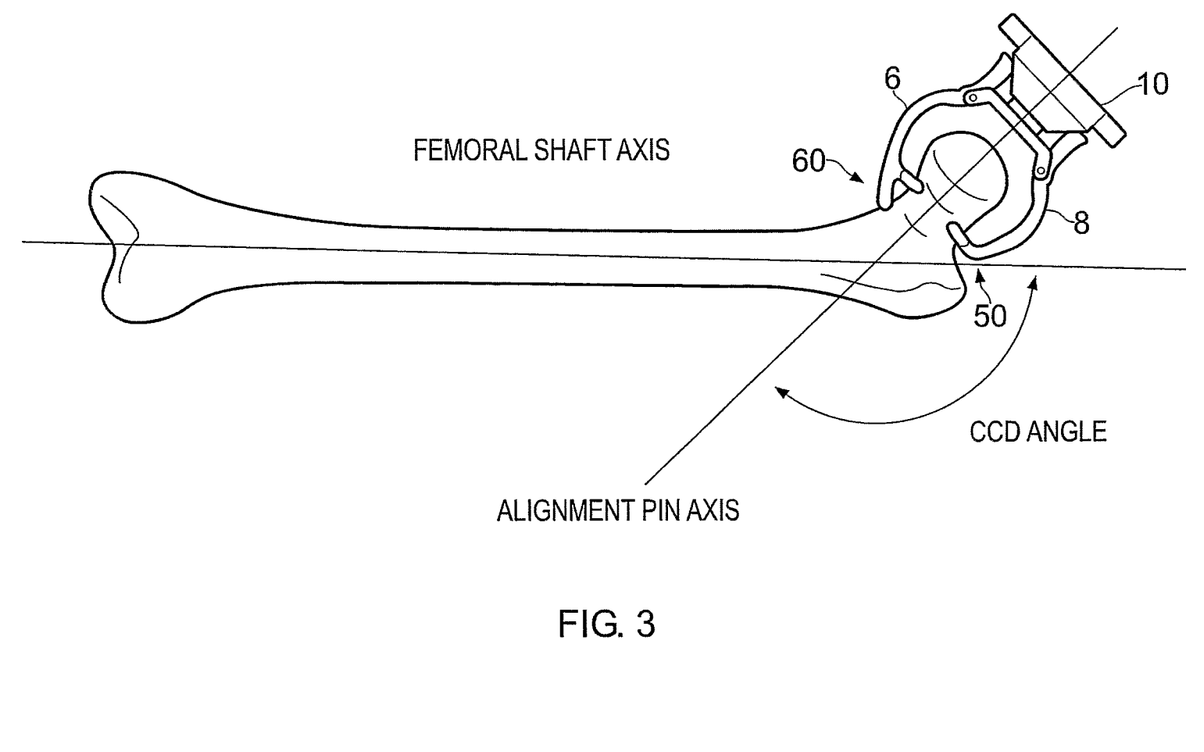
FIG. 3 is a side view of the instrument of FIG. 1 mounted on a femur.
Figure 4:
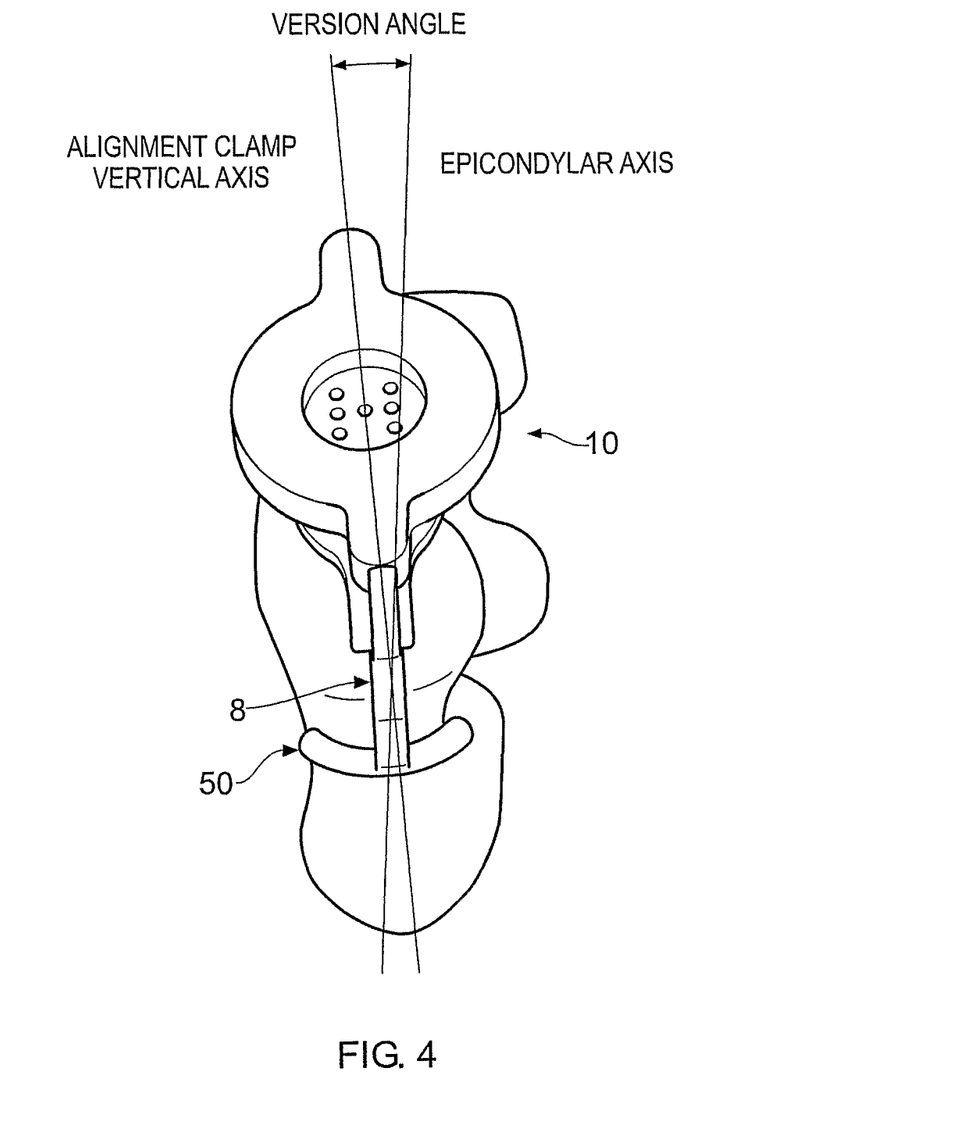
FIG. 4 is an end view of the instrument illustrated in FIG. 3.

With reference to FIGS. 3 and 4, the instrument 2 may be used to guide a femoral alignment pin during a femoral resurfacing procedure. Prior to use, the instrument 2 is prepared by unscrewing the nut 10, so as to allow free pivoting motion of the arms 6, 8. The instrument is then placed over the femoral head with the inferior arm 6 on the inferior side of the femoral neck and the superior arm 8 on the superior side of the femoral neck. The nut 10 is then screwed onto the post 14. As the nut 10 progresses proximally down the post 14, the engagement surface 78 of the nut 10 contacts the cam surfaces 72, 74 of the engagement portions 36, 38 of the arms 6, 8. Further proximal motion of the nut 10 forces the engagement portions 36, 38 of the arms 6, 8 apart, thus bringing the jaws 50, 60 of the arms 6, 8 into contact with the femoral neck. The nut 10 is screwed onto the post 14 until the jaws 50, 60 are firmly clamped around the femoral neck. The regions or points of contact provided by the three jaw elements 52, 64, 66 ensure a stable connection between the instrument and the bone.

With the instrument correctly mounted on the bone, the inferior, bifurcated jaw 60 provides a three dimensional reference of the calcar surface of the femoral neck. The superior jaw 50 provides a two dimensional reference of the superior surface of the femoral neck. The position at which the instrument centres itself on the femoral neck is thus determined by the inferior angle of the femoral neck (the calcar angle) and by the diameter of the femoral neck. The curvature of the arms 6, 8, the curvatures of the cam surfaces and engagement surface 72, 74, 78, and the orientation of the bores 90 are selected such that, with the instrument clamped in the manner described above, the axes of the bores 90 converge towards the centre of the femoral neck and are aligned at an optimal collodiaphyseal angle (the angle between the femoral neck and shaft) and optimal anteversion to guide the insertion of a femoral alignment pin. The provision of several bores 90, each having a slightly different orientation, allows a surgeon a certain flexibility, enabling the most appropriate orientation for a particular patient to be selected.

The invention claimed is:

1. An instrument for aligning a surgical tool on a femoral head and a femoral neck of a femur, the instrument comprising:
   a body portion having a threaded post fixed to the body portion and projecting proximally, along a longitudinal axis, from a proximal surface of the body portion,
   a first arm, and a second arm, the first arm and the second arm each pivotably connected to the body portion via a first fork and a second fork, respectively, extending from opposite sides of the post and fixed to the body portion, each of the first and second arms having a distal portion, a proximal portion, and a coupling portion located between the distal and proximal portions, each of the coupling portions being coupled to one of the opposing forks by a pivot pin, wherein the distal portion of each of the first arm and the second arm is curved along a length of the distal portion forming a concave bone facing surface, a distal end of the distal portion of the second arm including a bifurcated tab including two curved jaw elements for engaging the femoral neck, and a distal end of the distal portion of the first arm including a curved jaw for engaging the femoral neck, the proximal portion of each of the first arm and the second arm including a curved cam surface,
   the threaded post comprising at least a first bore and a second bore extending therethrough, the first bore having a first longitudinal axis differently aligned from a second longitudinal axis of the second bore, and the first and the second longitudinal axes are differently aligned from the longitudinal axis of the post; and
   a nut having a threaded bore configured to threadably engage the post, the nut including a frustoconical engagement surface that tapers outwardly from the threaded bore, the frustoconical engagement surface configured to engage the curved cam surfaces of the proximal portions of the first and second arms and causes the two curved jaw elements and the curved jaw of the first and second arms to engage a predetermined portion of the femoral neck upon threading the nut along the post,
   wherein when the first and second arms are clamped on the femoral neck, the first longitudinal axis and the second longitudinal axis converge towards a center portion of the femoral head at a point at a predetermined distance proximate the body portion, the point being located inside the femoral head when the instrument engages the femoral neck.

2. The instrument of claim 1, wherein the curved jaw of the first arm is curved to match a profile of the femoral neck.

3. The instrument of claim 1, wherein the first fork and the second fork each constrains lateral motion of the first arm and the second arm, respectively, towards and away from one another.

4. The instrument of claim 1, wherein longitudinal axes of a third bore and a fourth bore each converge at a different point from the first longitudinal axis and the second longitudinal axis.

5. The instrument of claim 1, wherein the post is configured to allow for drilling an alignment hole into the femoral neck of the femoral head.

6. A surgical instrument for aligning a surgical tool on a femoral head and a femoral neck of a femur, the surgical instrument comprising:
   a body portion having opposed forks and an intermediate annular flange having a proximal surface and a distal surface, a threaded post fixed to the body portion and projecting proximally, along a first longitudinal axis, from the proximal surface of the body portion, the post including a plurality of guide bores extending therethrough, at least two of the plurality of guide bores extending through the threaded post along longitudinal axes at different angles relative to each other and to the first longitudinal axis of the threaded post;
   a first arm and a second arm each pivotably coupled to one of the opposed forks of the body portion, each of the first and second arms having a distal portion, a proximal portion, and a coupling portion located between the distal and proximal portions, each of the coupling portions being coupled to one of the opposing forks by a pivot pin, wherein the distal portion of each of the first arm and the second arm is curved along a length of the distal portion forming a concave bone facing surface, a distal end of the distal portion of the second arm including a bifurcated tab including two curved jaw elements for engaging the femoral neck, and a distal end of the distal portion of the first arm including a curved jaw for engaging the femoral neck, the proximal portion of each of the first arm and the second arm including a curved cam surface; and
   a nut having a threaded bore configured to threadably engage the post, the nut including a frustoconical engagement surface that tapers outwardly from the threaded bore, the frustoconical engagement surface engages the curved cam surfaces of the proximal portions of the first and second arms and configured to urge the curved jaw of the first arm and the two curved jaw elements of the second arm together to contact the femoral neck upon threading the nut along the post,
   wherein the at least two of the plurality of guide bores are configured such that when the jaws of the first and second arms are in contact with the femoral neck, the longitudinal axes of the bores are aligned at a predetermined collodiaphyseal angle between the femoral neck and a shaft of the femur, and are aligned at a predetermined anteversion.

7. The surgical instrument of claim 6, wherein motion of the first arm and the second arm is restricted to a first direction in which the distal ends of the first and second arms move towards one another, and a second direction in which the distal ends of the first and second arms move apart.

8. The surgical instrument of claim 6, wherein the axes of the at least two of the plurality of guide bores converge inside the femoral neck bone when the surgical instrument is coupled to the femoral neck.

* * * * *